| United States Patent [19] | [11] Patent Number: 4,759,880 |
|---|---|
| Nicolaou et al. | [45] Date of Patent: Jul. 26, 1988 |

[54] ALKANOARACHIDONIC ACIDS

[75] Inventors: Kyriacos C. Nicolaou, Havertown; Nicos A. Petasis, Drexel Hill; Wen-Sen Li, Philadelphia; Tamara Ladduwahetty, Philadelphia; Jared L. Randall, Philadelphia; Stephen E. Webber, Philadelphia; Pedro E. Hernandez, Philadelphia, all of Pa.

[73] Assignee: Research Corporation, N.Y.

[21] Appl. No.: 655,196

[22] Filed: Sep. 27, 1984

[51] Int. Cl.[4] ............... C11C 1/00; C07C 33/05; C07C 47/21; A61K 31/045
[52] U.S. Cl. ............... 260/413; 260/410.9 R; 514/531; 514/559; 514/729; 514/703; 568/420; 568/700
[58] Field of Search ............ 260/413 L, 410.9 M, 260/410.9 R; 568/700, 420

[56] References Cited

U.S. PATENT DOCUMENTS

| 2,955,140 | 10/1960 | Hofer et al. | 568/700 |
| 3,972,907 | 8/1976 | Baran et al. | 260/413 L |
| 4,065,480 | 12/1977 | Peterson et al. | 568/700 |
| 4,086,280 | 4/1978 | Peterson et al. | 568/700 |
| 4,464,304 | 8/1984 | Porter et al. | 260/410.9 R |
| 4,515,727 | 5/1985 | Patterson, Jr. et al. | 260/410.9 R |
| 4,599,439 | 7/1986 | Misra | 568/700 |

*Primary Examiner*—J. E. Evans
*Attorney, Agent, or Firm*—Scully, Scott, Murphy & Presser

[57] ABSTRACT

A series of alkanoarachidonic acids have been prepared as modulators of the arachidonic acid cascade to increase the production of biologically desirable compounds and minimize the production of biologically undesirable compounds. Examples of desirable compounds in this respect comprise postaglandins and thromboxanes whereas undesirable compounds comprise the mono- and polyhydroxyarachidonic acids and leukotrienes. The alkanoarachidonic acids and their intermediates are of the general formula:

wherein $R_1 =$

—COO(lower alkyl)
—(lower alkylene) OH
—(lower alkylene) CHO
—CHO wherein $R_2 =$ —COO(lower alkyl)
—(lower alkylene) OH
—(lower alkylene) CHO
—CHO wherein $R_3 =$ —COO(lower alkyl)
—(lower alkylene) OH
—(lower alkylene) CHO
—CHO and at least one of X, Y, and Z is lower alkano and is hydrogen when not lower alkano; the esters and salts of the acids are also prepared. The acids, esters and salts may be used as anti-anaphylaxis or anti-thrombosis agents.

19 Claims, No Drawings

ALKANOARACHIDONIC ACIDS

SUMMARY OF THE INVENTION

The invention relates to new arachidonic acid derivatives which are particularly effective in minimizing anaphylaxis or thrombosis in treated hosts. The new derivatives are alkanoarachidonic acids.

Arachidonic acid is a naturally occurring substance found in animals and is enzymatically converted in vivo into other substances such as mono and polyhydroxy derivatives and leukotrienes by 5-lipoxygenase. The leukotrienes are directly implicated in anaphylaxis e.g. allergenic or asthmatic reactions. It has now been found that arachidonic acid may be modified to minimize or prevent its enzymatic conversion to leukotrienes or other products by blocking the 7, 10, or 13 bis-allylic positions on the arachidonic acid molecule by lower alkano groups. The arachidonic acid that has been modified in this fashion can then be administered to a mammalian host where it will compete with naturally occurring arachidonic acid or arachidonic acid receptor sites within the host. Enzymatic conversion of the modified arachidonic acid at these receptor sites will result in either minimal or no production of leukotrienes at the sites thereby minimizing or eliminating anaphylaxis manifested as allergenic or asthmatic symptoms.

Certain modified arachidonic acids are also anti-thrombosis agents.

The modification of the arachidonic acid may also be carried out to promote or inhibit the enzymatic conversion of the acid to compounds such as prostaglandins and thromboxanes.

DETAILED DESCRIPTION

Arachidonic acid is a substance that occurs naturally in and is enzymatically converted into other materials such as prostaglandins and thromboxanes by cycloxygenase or mono and polyhydroxy metabolites and leukotrienes by 5-lipoxygenase. The conversion of arachidonic acid, according to the major peroxidation pathways of the acid molecule, begins with an enzymatic abstraction of a hydrogen radical from the 7, 10, or 13 bis-allylic positions. The present invention comprises the discovery that by blocking one or more of these positions of arachidonic acid its enzymatic conversion to one or more of the products in the arachidonic acid cascade can be minimized or eliminated whereas the production of other products in the cascade can be increased. The present invention also relates to the discovery that by selectively blocking the various 7, 10, and 13 bis-allylic positions on the arachidonic acid molecule or various combinations of these positions, it is possible to promote the enzymatic conversion of the acid for the production of some compounds such as prostaglandins and thromboxanes and to minimize production of other compounds such as mono and polyhydroxy derivatives and leukotrienes. The various 7, 10 and 13 bis-allylic positions are blocked, according to this invention by an alkano group which is an alkylene chain, the termini of which are attached to a common carbon atom.

The present invention also relates to novel compounds comprising the modified arachidonic acids and the intermediates employed in their synthesis as well as a process for their manufacture. The compounds are generally of the formula:

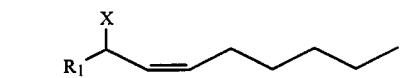

wherein $R_1$ =

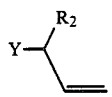

—COO(lower alkyl)
—(lower alkylene) OH
—(lower alkylene) CHO
—CHO wherein $R_2$ =

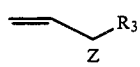

—COO(lower alkyl)
—(lower alkylene) OH
—(lower alkylene) CHO
—CHO wherein $R_3$ =

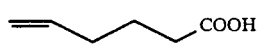

—COO(lower alkyl)
—(lower alkylene) OH
—(lower alkylene) CHO
—CHO and at least one of X, Y, and Z is lower alkano and is hydrogen when not lower alkano; provided that where Z is lower alkano at least one of X and Y is also lower alkano.

The terms "lower alkylene" and "lower alkyl" include for the purposes of this invention, alkyl and alkylene groups and their structural isomers having from one to about four carbon atoms whereas the expression, "lower alkano" is meant to include alkano groups having from two to about four carbon atoms.

The present invention also relates to a method for the prophylaxis and treatment of thrombosis or anaphylaxis e.g. allergies such as asthma with the substituted arachidonic acids, esters and salts. The arachidonic acids, esters or salts suitable in this regard i.e. the therapeutic agents of this invention are substituted in the 7, 10 or 13 positions or any combination thereof by a lower alkano group. The aforesaid substituted acids, esters or salts are administered to a mammalian host in an anti-anaphylaxis effective amount or an antithrombosis effective amount.

The therapeutic agents that comprise the esters are the lower alkyl esters of arachidonic acid (where lower alkyl has been defined herein previously), and the salts of archidonic acid are substituted in the 7, 10 or 13 position or any combination thereof by a lower alkano group. The esters and the salts in this respect comprise any ester or salt that is pharmaceutically acceptable and known in the art and include not only the alkali metal salts but also the alkaline earth salts and the various ammonium salts and amine salts or any combination of such esters and salts or any mixtures of said esters with said salts.

The enzymatic conversion of arachidonic acid to mono and polyhydroxy metabolites and leukotrienes by means of 5-lipoxygenase is a significant process in the arachidonic acid cascade since the leukotrienes themselves are implicated in anaphylaxis e.g. asthmatic attacks. When administering the lower alkano substituted arachidonic acids that have been substituted in any combination of the 7, 10, or 13 bis-allylic position to a host, they will be absorbed at the various receptor sites in the host that are implicated in anaphylaxis and will compete with naturally occurring arachidonic acid in the host for these receptor sites. Any 5-lipoxygenase acting on the modified arachidonic acid at the receptor sites will be inhibited so that the production of leukotrienes will either be minimized or eliminated and the anaphylactic reaction of the host lessened or prevented.

The various receptor sites for arachidonic acid in host mammals in some instances also act as receptor sites for the metabolites in the arachidonic acid cascade. The lower alkano substituted arachidonic acids of the present invention are capable of competing with these early metabolites for such receptor sites as well.

The method of preparing these compounds have been described by the inventors herein in J. Org. Chem. 48, 5400–5403 (1983) which is incorporated herein by reference.

The following examples are illustrative:

EXAMPLES

MONOETHANOARCHIDONIC ACIDS

A method for constructing the arachidonic acid skeleton of the monoethanocompounds 1–3 was devised. This retrosynthetic analysis disconnects each compound at the double bonds adjacent to the cyclopropane ring by retro-Wittig type operations leading to the common central fragment 7, the α-fragments 4–6 and the ω-fragments 8–10. As described below, this strategy was successfully executed after securing these fragments in stereochemically pure form by acetylene alkylation and selective hydrogenation techniques.

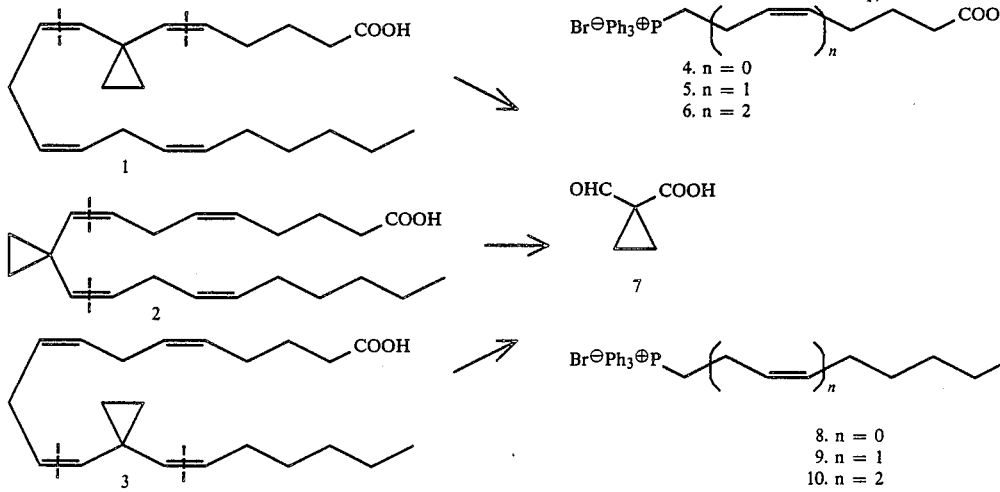

Alkylation of the lithioderivative (1.1 eq. nBuLi, THF, −78°→25°) of acetylene 11 with Br(CH$_2$)$_3$Cl (1.5 eq., 0°→25° C.) followed by cyanation (5 eq. NaCN, HMPA, 25° C.)[8] led to 12[9] (90%) which was desilylated (1.1 eq. nBu$_4$NF, THF, 25° C.) to 13, brominated (1.3 eq. CBr$_4$, 1.3 eq. Ph$_3$P, CH$_2$Cl$_2$, 0° C.)[10] to 14, hydrogenated (H$_2$, Lindlar catalyst, MeOH, 25° C.) and finally transformed to methylester 15 (1.2 eq. MeCOCl, MeOH, 0° C.) in 80% overall yield form 12. An alternative and shorter route to this fragment involved ortho-ester 16 known in the art, which was first converted to 17 in 80% yield by (a) metallation (1.3 eq. nBuLi, THF, 1.0 eq. TMEDA, −30° C.) (b) quenching with excess ethylene oxide and (c) hydrolysis (MeOH, 0.05 eq. PPTS, 25° C.) and then to 15 (95% overall) by Lindlar hydrogenation (CH$_2$Cl$_2$, 25° C.) and bromination as above (13→14). Conversion of 15 to the desired phosphonium salt 5 proceeded smoothly after hydrolysis of the ester (LiOH, THF-H$_2$O, 25° C., 95%) and heating (70° C.) with Ph$_3$P in MeCN (87%).

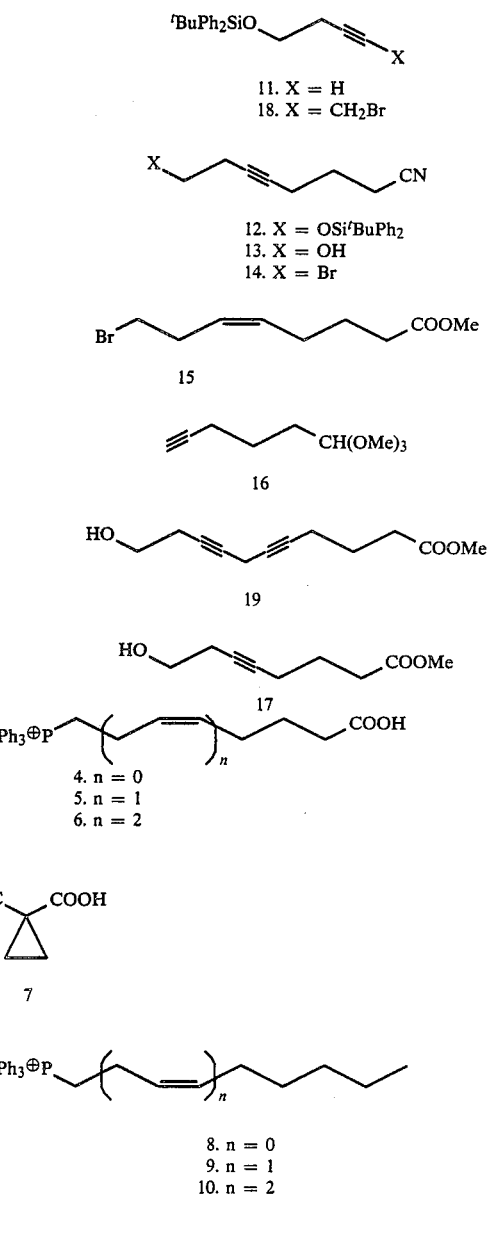

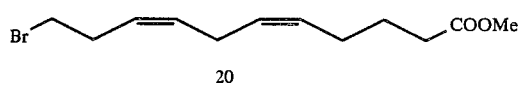

-continued

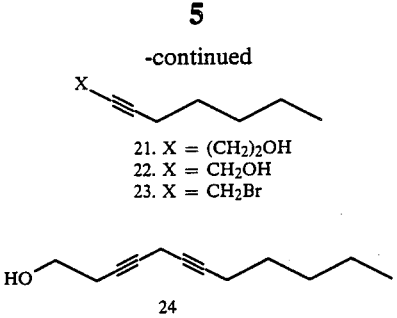

21. X = (CH₂)₂OH
22. X = CH₂OH
23. X = CH₂Br

HO⎯≡⎯≡⎯⎯⎯⎯⎯

24

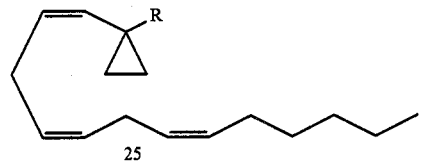

25 a. R = COOMe
b. R = CH₂OH
c. R = CHO

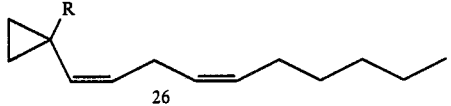

26

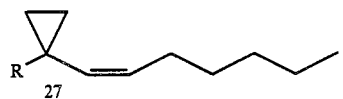

27

For the synthesis of 6, compound 11 was converted to bromide 18 (1.1 eq. nBuLi, THF, 0° C. followed by excess (CH₂O)$_n$, 25° C. (84%) and then bromination as in 13→14, 95%) which was then used to alkylate ortho-ester 16 (1.1 eq. nBuLi, 0.5 eq. CuI, THF, −78°→25° C.) an art known method leading, after hydrolysis (MeOH, 0.05 eq. CSA, 25° C.) and desilylation (as in 12→13) to intermediate 19 (68% overall from 18). The transformation of 19 to 6 proceeded cleanly as in 17→5.

As starting materials for the synthesis of 9 and 10, by known methods we used the commercially available acetylenic alcohols 21 and 22 which were subjected to similar methodology and with similar results. Noteworthy here, is the elongation of 22 to 24 via bromide 23 and direct reaction with 3-butyn-1-ol (1.5 eq.) pretreated with EtMgBr (2.8 eq.) and CuCl (2.0 eq.) in THF (0° C.) in over 80% yield despite the absence of any OH protection as shown in the prior art.

The crystalline cyclopropane derivative 7 was synthesized in large quantities by selective reduction (2.2 eq. DIBAL, CH₂Cl₂, −78° C. followed by acid workup, 85%) of the corresponding nitrile carboxylic acid, readily available, according to Singh and Danishefsky. *J Org. Chem.* 1975 40, 2969. This compound was chosen as an ideal source of the requisite building block with self-protecting functionality, thus avoiding extra protection-deprotection steps.

In coupling the three fragments towards the desired target molecules 1–3, we relied on the Wittig reaction and specific modifications of it which led predominantly to the required Z-geometry of the newly generated double bonds, in these circumstances made a highly demanding task due to the presence of the bulky cyclopropane ring. Indeed, condensation of the ylid derived from 10 (3.0 eq. 10, 3.0 eq. nBuLi, THF-HMPA (5:1), −78° C.) with the sodium salt of 7 (1.1 eq. NaH, THF-HMPA, (5:1) 0° C.), −78° 0° C.) check lens at 78° 25° C. led, after CH₂N₂ treatment, to 25a as a mixture of ca 8:1 Z:E ratio at the newly generated double bond (70%). Reduction of 25a (2.2 eq. DIBAL, CH₂Cl₂, −78° C., 90%) followed by chromatographic removal (flash column, silica ether-petroleum ether mixtures) of the undesired isomer and mild oxidation (1.2 eq. CrO₃, pyr. HCl, CH₂Cl₂, 25° C.[16] or 6.0 eq. SO₃ pyr., 10.0 eq. Et₃N, DMSO, 25° C.[17]) led to aldehyde 25c (90%). Finally, coupling of 25c with the standard PG ylid derived from 4 according to Bestmann's conditions (*Chem. Ber.*, 1976 109, 1694) (1.5 eq. 4, 3.0 eq. NaN(SiMe₃)₂, DME, 0°→25° C.) furnished 7, 7-ethanoarachidonic acid (1) in 70% yield.

Minor undesired isomers were removed by flash column chromatography (silica, ether-petroleum ether mixtures of the esterification product (CH₂N₂, ether, 0° C.), followed by recovery of the desired acid by hydrolysis (LiOH, THF, H₂O, 25° C.).

Similarly, 10,10-ethanoarachidonic acid (2) was constructed by (a) condensing the ylid derived from the phosphonium salt 9 (3.0 eq. 9, 3.0 eq. nBuLi, THF-HMPA (5:1), −78° C.) with the sodium salt of 7 (−78°→25° C.) to afford, after CH₂N₂ treatment, the methylester 26a (70% yield, Z:E ca 8:1) which was converted to aldehyde 26c as in 25a→25c. Attachment of the α-fragment 5, proceeded smoothly under basic conditions (2.0 eq. 5, 4.0 eq. NaN(SiMe₃)₂, HMPA, 25° C.) and led to 10,10-ethanoarachidonic acid (2) (70%).

Finally, condensation of aldehyde 7 with the ylid generated from 8 (1.5 eq. 8, 2.5 eq. ᵗBuOK, THF-HMPA (7:1), 25° C., then add 7 at −78°→25° C.) gave, after esterification (CH₂N₂), 27a in 85% yield and Z:E ratio ca 91:9. After reduction, separation of Z and E isomers using a flash column previously described and oxidation as in 25a→25c above, the aldehyde 27c was obtained and reacted with the ylid corresponding to 6 (2 eq. 6, 4.0 eq. NaN(SiMe₃)₂, HMPA, 25° C.) leading to 13,13-ethanoarachidonic acid (3) in 80% yield.

An alternative and completely stereo-controlled total synthesis of 13,13-ethanoarachidonic acid (3) based on the acetylene unit as a stereoselective precursor for each of the four ZI double bonds was also developed. Thus, starting with the methylester of 7, (CH₂N₂, 0° C., 100%) the dibromoolefin 28 was prepared (2.0 eq. CBr₄, 2.09 eq. Ph₃P, CH₂Cl₂, 0° C., 70%)[20] (Corey et. al. *Tetrahedron Lett.*, 1972, 3769 Nagaoka et. al. *Tetrahedron* 1981, 37, 3873.) and subjected to the following transformations: (a) reduction to 29 (2.2 eq. DIBAL, CH₂Cl₂, −78° C., 80%); (b) silylation to 30 (1.2 eq. ᵗBuMe₂SiCl, 1.3 eq. Et₃N, 0.04 eq. DMAP, CH₂Cl₂, 90%); (c) metallation (2.2 eq. nBuLi, THF, −78° C.) followed by quenching with excess I (CH₂)₄ *CH₃* (−78°→reflux) to give 31 (60%); (d) mild hydrogenation (H₂, Pd/BaSO₄ catalyst, pyridine, 25° C.)[21] to 32 (100%) and (e) desilylation and oxidation as described above to afford 27e. Similar chemistry was then applied to convert 27c to 35: 27c 33 (as in the synthesis of 28), 33→34 (2.2 eq. nBuLi, THF, −78° C. then excess ClCOOEt, 99%), 34→35 (as in 28→29, 92%).

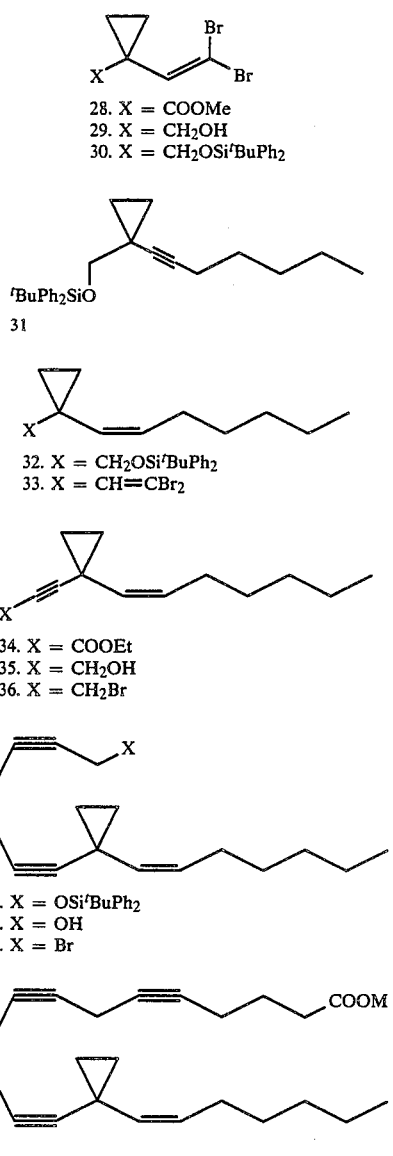

Conversion of 35 to the bromide 36 (as in 13→14, 100%), followed by coupling with the tert-butyldiphenylsilyl ether of 2-propyn-1-ol (1.1 eq. nBuLi, 0.5 eq. CuI, THF, −78° 25° C., 91%) led to 37, which was transformed to the bromide 39 by deprotection (75%) and bromination (as in 13→14, 92%). Finally, coupling of this bromide with 16 as above (16→19) led to 40 (88% yield) which was hydrogenated (H$_2$, Linlar catalyst, ethyl acetate, 25° C., 65%) affording the methylester of 3.

Biological studies to define the profiles of these compounds reveal interesting and selective properties including, in vitro inhibition of SRS-A biosynthesis, 5-lipoxygenase inhibition, phospholiphase A$_2$ inhibition and antithrombotic activity. For example, 7,7-ethanoarachidonic acid (1) exhibited the following activities: (a) At 10M: 82±6% inhibition of ionophore A23187-induced SRS-A biosynthesis in rat peritoneal cells, (b) At 100 μM 86% inhibition of conversion of $^{14}$C-AA to $^{14}$C-5-HETE in super natant from RBL-1 cells, (c) AT 100 μM: 100% inhibition (1C$_{50}$=18) of phospholipase A$_2$ (from Naja snake venom, liposomes of dipalmitoylphosphatidyulcholine as substrate) and (d) At 80 μM: 50% inhibition of AA-induced platelet aggregration (human gel-filtered platelet suspension containing 0.2% albumin).

EXAMPLES
POLYETHANOARACHIDONIC ACIDS

The synthesis of these modified arachidonic acids proceeded along lines indicated by the disconnections at all double bonds adjacent to cyclopropanes. The chemistry utilized for the synthesis of these members of the series is similar to that outlined in the preceding examples with the important introduction of the new cyclopropyl reagent 6$^a$. This phosphonium salt was prepared from 5$^a$ as follows: (a) CH$_2$N$_2$Et$_2$O, 0° C., 100%, (b) 0.6 eq. NaBH$_4$, MeOH, −35° C., 75%, (c) 1.3 eq. CBr$_4$, 1.5 eq. Ph$_3$P, CH$_2$Cl$_2$ 0° C., 90%, (d) 1.3 eq. Ph$_3$P, MeCN, 65° C., 90%. As shown below, 6$^a$ is a convenient means for attachment of the cyclopropyl unit, and should prove to be of general use for this purpose.

Condensation of the ylid derived from 6$^a$ (1.2 eq. of 6$^a$, 1.1 eq. NaN(SiMe$_3$)$_2$, (Bestmann et al., supra,) DME-HMPA (4:1), −30°→25° C.) with aldehydes 7$^a$ and 10$^a$ proceeded in 65–86% yields and Z:E ratios ranging from 55:45 to 85:15, furnishing methyl esters 8$^a$ and 11$^a$ respectively. These rather poor Z:E ratios can be attributed to the bulky cyclopropane substituents on both sites of the newly formed double bond. Reduction of methylester 8$^a$ (2.2 eq. DIBAL, CH$_2$Cl$_2$, −78° C., 94%) to the corresponding alcohol, followed chromatographic removal as described previously of the undesired E isomer and oxidation (6 eq. SO$_3$.pry., 10 eq. Et$_3$N, DMSO, 25° C., 90%) gave aldehyde 9$^a$. Condensation of 9$^a$ with the standard prostaglandin ylid (5.0 eq. Br$^-$Ph$_3$P$^+$(CH$_2$)$_4$COOH, 9.0 eq. NaN(SiMe$_3$)$_2$, DME, 0° C.) led to 7,7,10,10-diethanoarachidonic acid (1$^a$, →70%) in high stereochemical purity. Trace amounts of isomeric materials were chromatographically removed at the methylester stage (CH$_2$N$_2$, 0° C.) from where the acid could easily be regenerated (LiOH, THF-H$_2$), 25° C.).

10,10,13,13-Diethanoarachidonic acid (2$^a$), was constructed form methylester 11$^a$ by similar reactions and in comparable yields. Thus, sequence 11$^a$→12$^a$ was carried out as in 8$^a$→9$^a$ in ca 80% overall yield. The final coupling of 12$^a$ with Wittig reagent 13$^a$ was performed under slightly different conditions (NaN(SiMe$_3$)$_2$, HMPA, 25° C., 70%), leading to 2$^a$ in high Z to E ratio.

The synthesis of 7,7,13,13-diethanoarachidonic acid (3$^a$), was initiated again with aldehyde 10$^a$ which was now condensed with the ylid derived from 14$^a$ (NaN(SiMe$_3$)$_2$, DME, 0°→25° C.) to form 15$^a$ (96%, ca 20:1 Z:E). Transformation of 15 to phosphonium salt 18$^a$ (Ph$_3$P, MeCN, 70° C.) proceeded conventionally via the alcohol 16$^a$ (nBu$_4$NF, THF, 25° C.), chromatographic removal of undesired E isomer, and bromide 17$^a$ (1.3 eq. CBr$_4$, 1.5 eq. Ph$_3$P, CH$_2$Cl$_2$, 0° C.). Condensation of the phosphorane derived from 18$^a$ (NaN(SiMe$_3$)$_2$, DME, 0° C.) with the sodium salt of 5$^a$ led, after CH$_2$N$_2$ treatment, to methylester 19$^a$ (70%, ca 20:1 Z:E ratio). Reduction (2.2 eq. DIBAL, CH$_2$Cl$_2$, 0° C.) of 19$^a$ followed by isomer separation utilizing a flash column method previously described (90% pure Z isomer) and oxidation as in 8$^a$→9$^a$ furnished 20$^a$ (90%)

which was coupled with excess of the PG ylid (Br⁻Ph₃P(CH₂)₄COOH, 2 eq. NaN(SiMe₃)₂, DME-HMPA, 3:1, 0°→25° C.) leading to the desired acid 3ᵃ in 82% yield. Isomeric materials were chromatographically removed as previously described.

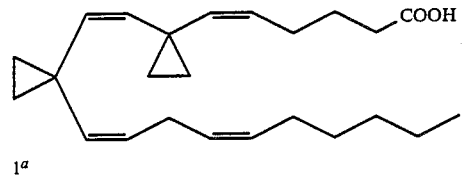

1ᵃ

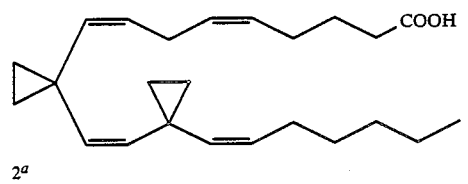

2ᵃ

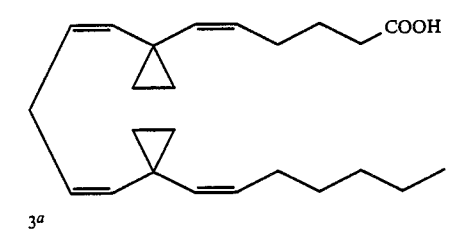

3ᵃ

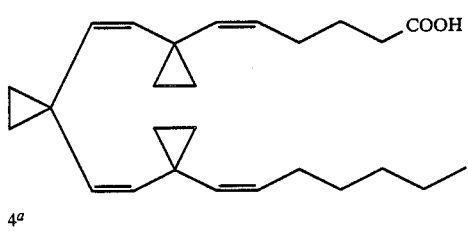

4ᵃ

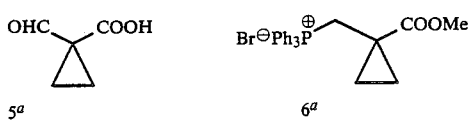

5ᵃ      6ᵃ

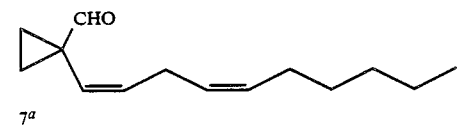

7ᵃ

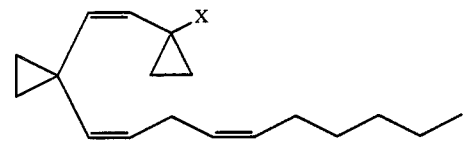

8ᵃ. X = COOMe
9ᵃ. X = CHO

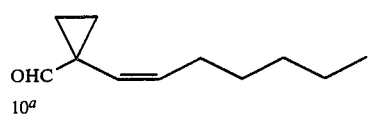

10ᵃ

-continued

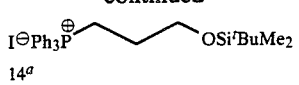

14ᵃ

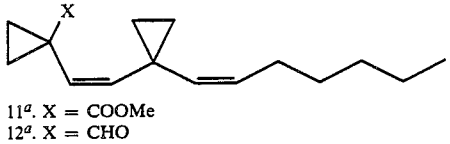

11ᵃ. X = COOMe
12ᵃ. X = CHO

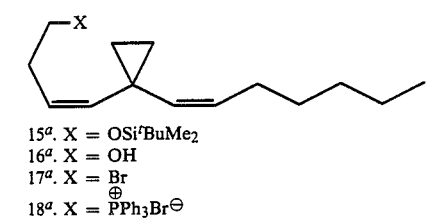

15ᵃ. X = OSi^tBuMe₂
16ᵃ. X = OH
17ᵃ. X = Br
18ᵃ. X = ⁺PPh₃Br⁻

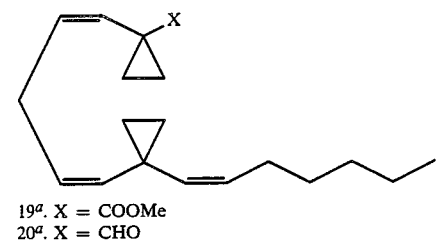

19ᵃ. X = COOMe
20ᵃ. X = CHO

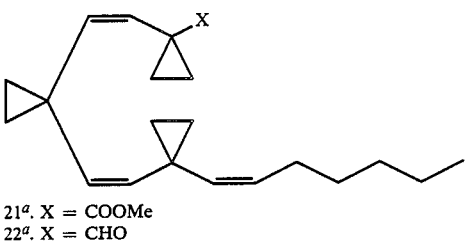

21ᵃ. X = COOMe
22ᵃ. X = CHO

Finally, condensation of 12ᵃ with the yield of 6ᵃ (NaN(SiME₃)₂, THF-HMPA, 3:1, −30°→25° C.) gave 21ᵃ (81% yield, ca 1:1 Z:E ratio). Transformation of 21ᵃ to 22ᵃ as in 8ᵃ→9ᵃ (chromatographic separation at the alcohol stage) followed by coupling with the standard PG ylid under the above-mentioned conditions led to 7,7,10,10,13,13-ethanoarachidonic acid (4ᵃ) (90% yield). Again, isomeric materials were chromatographically removed as previously described.

The esters disclosed herein, such as 8a, 11a, 19a or 21a, may be converted to the corresponding alcohol by reaction with lithium aluminum hydride in a manner known in the art.

Extensive biological investigations of these polyethanoarachidonic acids and their methylesters suggest powerful modulatory properties within the AA cascade, including lipoxygenase inhibitory activities. For example, 10,10,13,13-diethanoarachidonic acid (3ᵃ) at 40 μM induced a greater than a two fold increase in the arachidonic acid-induced production of malondialdehyde (MDA) in intact human platelets, indicating potent and specific inhibition of 12-lipoxygenase.

The lower alkano substituted arachidonic acids, esters, and salts of this invention i.e. the therapeutic agents of this invention may be administered alone or in combination with pharmaceutically-acceptable carriers, to hosts (e.g. mammals) as anti-anaphylaxis or anti-thrombosis compounds the portion of which is determined by the solubility and chemical nature of the compound, chosen route of administration and standard pharmaceutical practice. For example, they may be administered orally in the form of tablets, pills or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

When given orally, the therapeutic doses of the compounds of the present invention are generally in the range of from about 4 to about 450 mg/kg/day depending upon the particular mammalian host and the particular effect desired, such as anti-anaphylaxis or anti-thrombosis. When given by parenterally, the compounds are administered generally in dosages of, for example, 0.5 to about 15 mg/kg/day also depending upon the host and effect desired.

Although the invention has been described by reference to some embodiments, it it not intended that the novel compositions and method be limited thereby but that modifications thereof are intended to be included as falling within the broad scope and spirit the foregoing disclosure and the following claims.

What is claimed is:

1. A compound of the formula:

wherein $R_1$ =

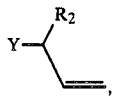

—COO (lower alkyl),
—(lower alkylene) OH,
—(lower alkylene) CHO, or
—CHO;

wherein $R_2$ =

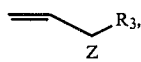

—COO (lower alkyl),

-continued
—(lower alkylene) OH,
—(lower alkylene) CHO, or
—CHO;

wherein $R_3$ =

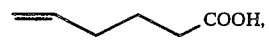

—COO (lower alkyl),
—(lower alkylene) OH,
—(lower alkylene) CHO, or
—CHO;

and at least one of X, Y and Z is ethano and is hydrogen when not ethano; provided that when Z is ethano, at least one of X and Y is also ethano.

2. A compound having the formula:

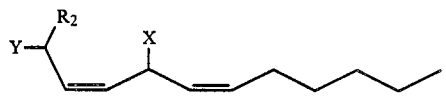

wherein $R_2$ =

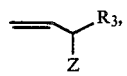

—COO (lower alkyl),
—(lower alkylene) OH,
—(lower alkylene) CHO, or
—CHO;

wherein $R_3$ =

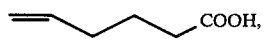

—COO (lower alkyl),
—(lower alkylene) OH,
—(lower alkylene) CHO, or
—CHO;

and at least one of X, Y and Z is ethano and is hydrogen when not ethano; provided that when Z is ethano, at least one of X and Y is also ethano.

3. The compound of claim 2 wherein $R_2$ =
—COO (lower alkyl),
—(lower alkylene) OH,
—(lower alkylene) CHO, or
—CHO.

4. A compound having the formula:

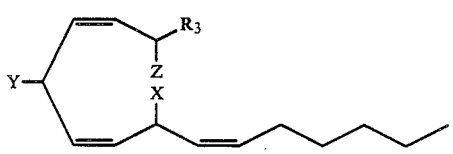

wherein $R_3$ =

—COO (lower alkyl),
-(lower alkylene) OH,
-(lower alkylene) CHO, or
—CHO;

and at least one of X, Y and Z is ethano and is hydrogen when not ethano; with the exception that when Z is ethano, at least one of X and Y is also ethano.

5. The compound of claim 4 wherein $R_3$ =
—COO (lower alkyl),
—(lower alkylene) OH, —(lower alkylene) CHO, or
—CHO.

6. A compound of the formula:

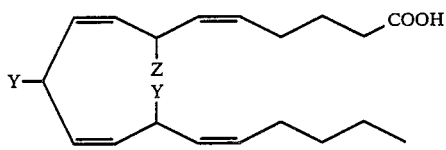

wherein at least one of X, Y and Z is ethano and is hydrogen when not ethano with the exception that where Z is ethano, at least one of X and Y is also ethano and the lower alkyl esters thereof and the salts thereof.

7. The compound of claim 1 having the formula

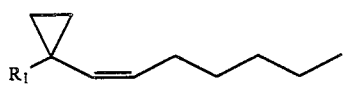

wherein $R_1 =$
—COO (lower alkyl),
—(lower alkylene) OH,
—(lower alkylene) CHO, or
—CHO.

8. The compound of claim 1 having the formula

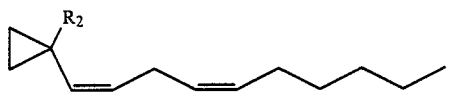

wherein $R_2 =$
—COO (lower alkyl),
—(lower alkylene) OH,
—(lower alkylene) CHO, or
—CHO.

9. The compound of claim 6 having the formula

10. The compound of claim 6 having the formula

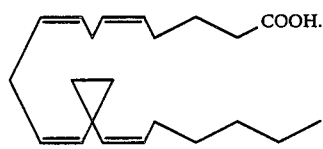

11. The compound of claim 4 having the formula

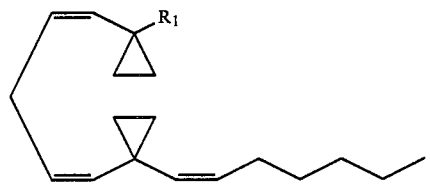

wherein $R_1 =$
—COO (lower alkyl),
—(lower alkylene) OH,
—(lower alkylene) CHO, or
—CHO.

12. The compound of claim 4 having the formula

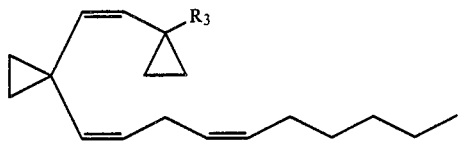

wherein $R_3 =$
—COO (lower alkyl),
—(lower alkylene) OH,
(lower alkylene) CHO, or
—CHO.

13. The compound of claim 4 having the formula

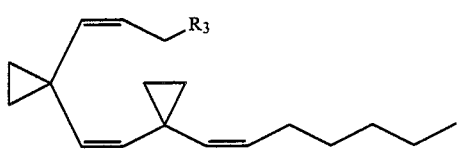

wherein $R_3 =$
—COO (lower alkyl),
—(lower alkylene) OH,
—(lower alkylene) CHO, or
—CHO.

14. The compound of claim 4 having the formula

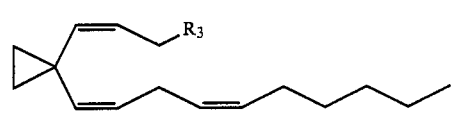

wherein $R_3 =$
—COO (lower alkyl),
—(lower alkylene) OH,
—(lower alkylene) CHO, or
—CHO.

15. The compound of claim 4 having the formula

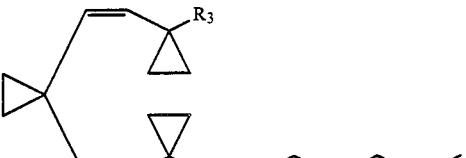

wherein $R_3 =$
—COO (lower alkyl),
—(lower alkylene) OH,
—(lower alkylene) CHO, or
—CHO.

16. The compound of claim 6 having the formula

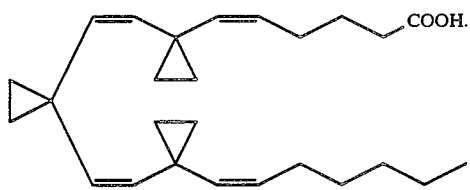
17. The compound of claim 6 having the formula
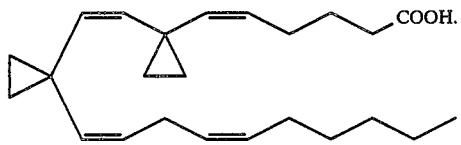
18. The compound of claim 6 having the formula
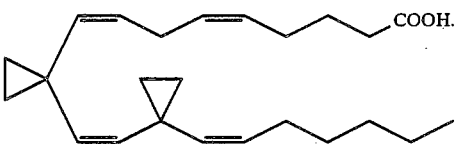
19. The compound of claim 6 having the formula
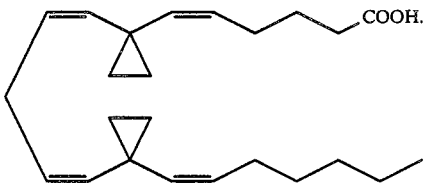
* * * * *

UNITED STATES PATENT AND TRADEMARK OFFICE
CERTIFICATE OF CORRECTION

PATENT NO. : 4,759,880
DATED : July 26, 1988
INVENTOR(S) : K. C. Nicolaou, et al.

It is certified that error appears in the above-identified patent and that said Letters Patent is hereby corrected as shown below:

Column 1, line 22: "acid or" should read as --acid for--

Signed and Sealed this

Twentieth Day of March, 1990

Attest:

JEFFREY M. SAMUELS

*Attesting Officer*  *Acting Commissioner of Patents and Trademarks*